(12) United States Patent
Bednarski et al.

(10) Patent No.: US 10,772,562 B2
(45) Date of Patent: Sep. 15, 2020

(54) METHOD FOR MONITORING NON-INVASIVE ARTERIAL OXYGEN SATURATION, PULSE RATE AND DETECTION OF CARBOXYHEMOGLOBIN

(71) Applicants: William Leon Bednarski, Tahoma, CA (US); Donald Edward Bebout, Berkeley, CA (US)

(72) Inventors: William Leon Bednarski, Tahoma, CA (US); Donald Edward Bebout, Berkeley, CA (US)

(73) Assignee: TheraTactics Inc, Cody, WY (US)

( * ) Notice: Subject to any disclaimer, the term of this patent is extended or adjusted under 35 U.S.C. 154(b) by 86 days.

(21) Appl. No.: 15/612,933

(22) Filed: Jun. 2, 2017

(65) Prior Publication Data
US 2018/0344247 A1    Dec. 6, 2018

Related U.S. Application Data

(60) Provisional application No. 62/349,588, filed on Jun. 13, 2016.

(51) Int. Cl.
*A61B 5/00* (2006.01)
*A61B 5/1455* (2006.01)
(Continued)

(52) U.S. Cl.
CPC .......... *A61B 5/6803* (2013.01); *A61B 5/0022* (2013.01); *A61B 5/0205* (2013.01); *A61B 5/0261* (2013.01); *A61B 5/02433* (2013.01); *A61B 5/14546* (2013.01); *A61B 5/14552* (2013.01); *A61B 5/14553* (2013.01); *A61B 5/6843* (2013.01); *A61B 5/7221* (2013.01); *A61B 5/7282* (2013.01);
(Continued)

(58) Field of Classification Search
CPC ... A61B 5/6803; A61B 5/7221; A61B 5/7282; A61B 5/7445; A61B 5/0022; A61B 5/6843; A61B 5/02433; A61B 5/14553; A61B 5/0205; A61B 5/0261; A61B 5/14546; A61B 5/14552; A61B 2562/0238; A61B 2562/227; A61B 2560/0475; A61B 2560/0214; A61B 2560/0257; A61B 2503/22
See application file for complete search history.

*Primary Examiner* — Navin Nathnithithadha
*Assistant Examiner* — Andrey Shostak
(74) *Attorney, Agent, or Firm* — Barry Choobin; Patent 360

(57) ABSTRACT

The various embodiments herein disclose a method for monitoring non-invasive arterial oxygen saturation ($SpO_2$), pulse rate (PR) and detecting level of carboxyhaemoglobin (COHb) in a blood flow of an aircraft pilot during an in-flight condition for detection of symptoms of hypoxia. The method comprises detection of an artery microcirculation of blood in forehead of the aircraft pilot by using an infrared (IR) photometric technique. A pulse oximetry (PO) reflectance sensor is installed over the detected artery with microcirculation in the forehead. The values of AI, VI and GI are combined with a signal strength and a signal quality of the PO sensor to calculate a final weighted index of confidence for $SpO_2$ ($CI_{sat}$) and PR ($CI_{pr}$) measurements. The measured values of $CI_{sat}$ and $CI_{pr}$ are implemented to calculate an overall weighted confidence index (CI) to determines an accuracy of measurements of $SpO_2$ and PR.

11 Claims, 4 Drawing Sheets

(51) Int. Cl.
A61B 5/145 (2006.01)
A61B 5/026 (2006.01)
A61B 5/0205 (2006.01)
A61B 5/024 (2006.01)

(52) U.S. Cl.
CPC ........ *A61B 5/7445* (2013.01); *A61B 2503/22* (2013.01); *A61B 2560/0214* (2013.01); *A61B 2560/0257* (2013.01); *A61B 2560/0475* (2013.01); *A61B 2562/0238* (2013.01); *A61B 2562/227* (2013.01)

METHOD FOR MONITORING NON-INVASIVE ARTERIAL OXYGEN SATURATION, PULSE RATE AND DETECTION OF CARBOXYHEMOGLOBIN

BACKGROUND

Technical Field of Invention

The embodiments herein generally relate to a method of in-flight pilot health monitoring and particularly relate to a method for monitoring a non-invasive arterial oxygen saturation, a pulse rate (PR) and detecting a carboxyhaemoglobin (COHb) of an aircraft pilot during in-flight conditions.

DESCRIPTION OF RELATED ART

Lack of oxygen is the greatest single danger to man at high altitudes, despite the importance of pressure and temperatures. The shortage of oxygen in a human body results in a condition called hypoxia, which means oxygen starvation. When a pilot inhales air at high altitudes, there isn't enough oxygen pressure to force adequate amounts of oxygen through the membranes of the lungs into the blood stream, so that it can be carried to the tissues of the body. The function of various organs, including the brain, is then starts to get impaired. The hypoxia scenario happens mainly during flights under high-G manoeuvres sometimes results into fatal pilot conditions. For e.g. during a time frame from 2008-2012, a F-22 Raptor (a fifth-generation fighter jet of United States) community experienced several unexplained hypoxia conditions like physiologic incidents including a cluster of four at one operating location that occurred during a 6-day period (Apr. 28-May 3, 2011). Following an F-22 fatal mishap on Nov. 16, 2010 that was reported as unexplained and the cluster of previously mentioned events, Air Combat Command (ACC) directed a fleet wide F-22 strategic pause (grounding) from May 3, 2011-Sep. 21, 2011. In January 2012, an ACC-led F-22 Life Support Systems Task Force identified several root causes and potential contributors to the incidents. Testing in April-May 2012 at Brooks Air Force Base showed that one of the key contributors was a valve on the Combat Edge Vest (CEV), which is designed to pressurize the CEV during high-G manoeuvres to improve pilot G-tolerance, and provide counter chest pressure protection in the event of rapid decompression at high altitude. After May 3, 2011, F-22 Raptors were allowed back into service but with a very limited flight envelope. On Apr. 4, 2013, F-22's that had been equipped with emergency backup oxygen systems (ABOS—automatic backup oxygen system) were allowed back to unrestricted flight status. However, another 11-unexplained hypoxia related incidents occurred after the grounding showing that the rate had not changed. In fact, Navy documents recorded 297 hypoxia related incidents from May 2010 to October 2015, a number that is significantly rising. Possible reasons for the increase may include increased pilot awareness, less incentive to under report and improved training of pilots to recognize hypoxia related symptoms.

Although the problem was slightly rectified in F-22 Raptor fighter jet by allowing additional life support system but the problems of oxygen deprivation and unexplained hypoxia like physiologic events still affect pilots in jet aircrafts. Most cases of hypoxia get undetected due to lack of a reliable and accurate data during in-flight conditions.

In the view of foregoing, there is a need for a method for monitoring non-invasive arterial oxygen saturation, pulse rate (PR) and detection of carboxyhaemoglobin (COHb) of an aircraft pilot during in-flight conditions. Also, there is a need for a method to provide an alert after a detection of reduction of oxygen in a pilot respiratory organ below a predetermined level resulting into a hypoxia.

The above-mentioned shortcomings, disadvantages and problems are addressed herein, as detailed below.

OBJECT OF THE INVENTION

The primary object of the embodiments herein is to provide a method for monitoring non-invasive arterial oxygen saturation, pulse rate (PR) and detection of carboxyhaemoglobin (COHb) of an aircraft pilot during in-flight conditions.

Another object of the embodiments herein is to provide a method to provide an alert after a detection of reduction of oxygen in a pilot respiratory organ below a predetermined level resulting into a hypoxia.

Yet another object of the embodiments herein is to provide a method for on-board installation of a sensor at a body skin for efficient detection of the carboxyhaemoglobin (COHb) of an aircraft pilot.

These and other objects and advantages of the embodiments herein will become readily apparent from the following detailed description taken in conjunction with the accompanied drawings.

SUMMARY OF THE INVENTION

The various embodiments herein disclose a method for monitoring non-invasive arterial oxygen saturation ($SpO_2$), pulse rate (PR) and detecting level of carboxyhaemoglobin (COHb) in a blood flow of an aircraft pilot during an in-flight condition for detection of symptoms of hypoxia. The method comprises detection of an artery microcirculation of blood in forehead of the aircraft pilot by using an infrared (IR) photometric technique. A pulse oximetry (PO) reflectance sensor is installed over the detected artery with microcirculation in the forehead. The PO sensor is installed in a headgear of the aircraft pilot. The method further comprises creation of indices corresponding to altitude (AI), vibration (VI) and gravitation (GI) under controlled conditions and varying conditions of hypobaria. A scale is designed on the basis of the values of the AI, VI and GI. The values of AI, VI and GI are combined with a signal strength and a signal quality of the PO sensor to calculate a final weighted index of confidence for $SpO_2(CI_{sat})$ and PR ($CI_{pr}$) measurements. The measured values of $CI_{sat}$ and $CI_{pr}$ are implemented to calculate an overall weighted confidence index (CI). The value of the weighted CI determines an accuracy of measurements of $SpO_2$ and PR.

According to one embodiment herein, the scale comprises a highest value of 1 resembling accurate functioning of the PO sensor and a lowest value of 0 resembling failure of the PO sensor.

According to one embodiment herein, each of the AI, VI and GI is weighted according to a magnitude of decrease in accuracy between 1 and 0.

According to one embodiment herein, a detection and measurement of SpO2, PR and CoHb is done through a central unit, a PO reflectance sensor and an air bladder.

According to one embodiment herein, the central unit comprises a Pulse Oximetry board, a barometer, an accelerometer, a data storage module and a rechargeable battery unit.

According to one embodiment herein, the central unit comprises a data output port and a connector to the PO reflectance sensor.

According to one embodiment herein, the method further comprises a computer readable program to assess rapid changes in gravitational forces in multiple directions simultaneously. The changes affect an accuracy to calculate the vibration index (VI).

According to one embodiment herein, the method further comprises a computer readable program and a barometer to measure a cabin pressure. A change in a cabin pressure affects an accuracy to calculate the altitude index (AI).

According to one embodiment herein, the method further comprises a three-dimensional accelerometer and a computer readable program to measure gravitational forces in at-least three directions (Gx, Gy and Gz. A magnitude of gravitational forces affects an accuracy to calculate the gravitational index (GI).

According to one embodiment herein, a pressure in the air bladder is adjusted on the basis of changes in gravitational forces in at-least three directions.

According to one embodiment herein, the method further comprises an early warning alarm. The early warning alarm is activated as an absolute value of the AI, GI and VI reaches a threshold point.

According to one embodiment herein, a data is collected through the PO sensor, stored and evaluated post flight, wherein the data is calculated in a real time and transmitted live to a ground control station and to the pilot via a heads-up display.

These and other aspects of the embodiments herein will be better appreciated and understood when considered in conjunction with the following description and the accompanied drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The other objects, features and advantages will occur to those skilled in the art from the following description of the preferred embodiment and the accompanied drawings in which.

DETAILED DESCRIPTION OF THE DRAWINGS

In the following detailed description, a reference is made to the accompanied drawings that form a part hereof, and in which the specific embodiments that may be practiced is shown by way of illustration. The embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

Figure 1:
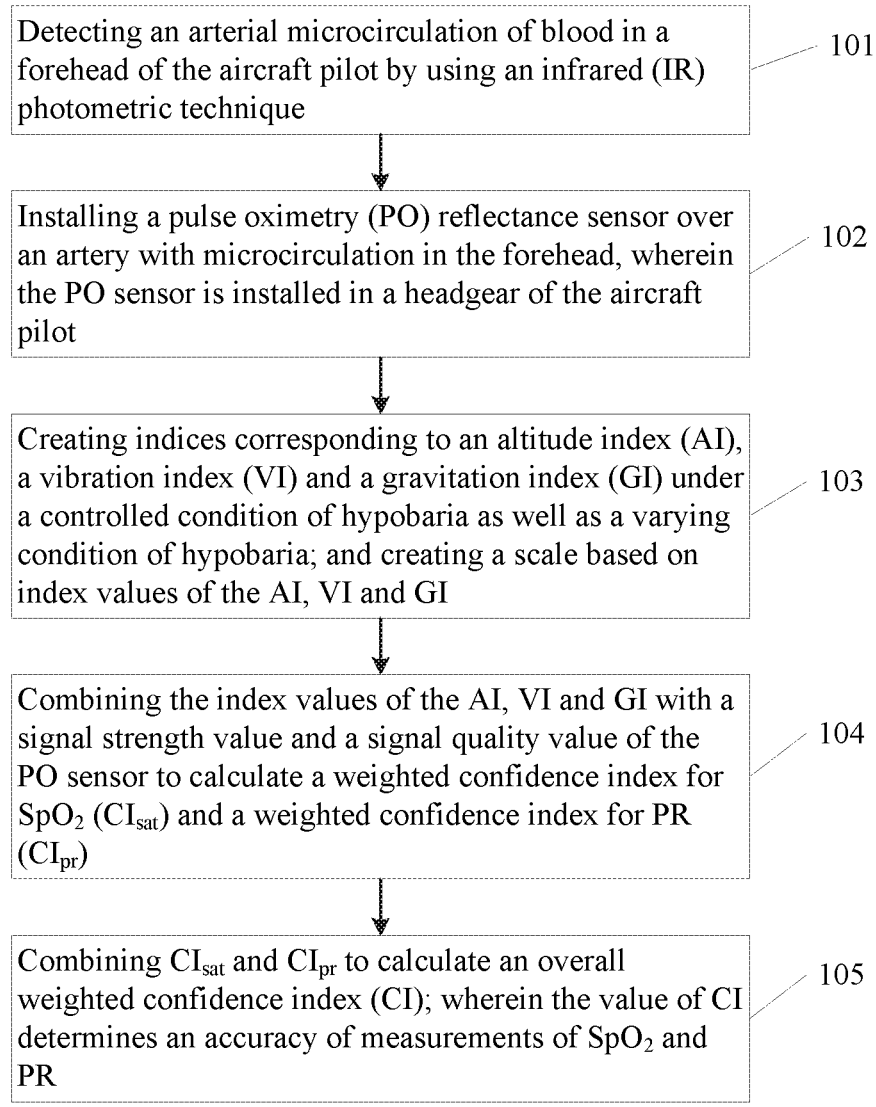
FIG. 1 illustrates a method for monitoring a non-invasive arterial oxygen saturation ($SpO_2$), a pulse rate (PR) and detecting a level of carboxyhaemoglobin (COHb) in a blood flow of an aircraft pilot during an in-flight condition, according to one embodiment herein.

FIG. 1 illustrates a method for monitoring a non-invasive arterial oxygen saturation ($SpO_2$), a pulse rate (PR) and detecting a level of carboxyhaemoglobin (COHb) in a blood flow of an aircraft pilot during an in-flight condition, according to one embodiment herein. With respect to FIG. 1, the method comprises detection of an artery microcirculation of blood in forehead of the aircraft pilot by using an infrared (IR) photometric technique (101). A pulse oximetry (PO) reflectance sensor is installed over the detected artery with microcirculation in the forehead (102). The PO sensor is installed in a headgear of the aircraft pilot. The method further comprises creation of indices corresponding to altitude (AI), vibration (VI) and gravitation (GI) under controlled conditions and varying conditions of hypobaria (103). A scale is designed on the basis of the values of the AI, VI and GI. The values of AI, VI and GI are combined with a signal strength and a signal quality of the PO sensor to calculate a final weighted index of confidence for $SpO_2$ ($CI_{sat}$) and PR ($CI_{pr}$) measurements (104). The measured values of $CI_{sat}$ and $CI_{pr}$ are implemented to calculate an overall weighted confidence index (CI) (105). The value of the weighted CI determines an accuracy of measurements of $SpO_2$ and PR.

According to one embodiment herein, the scale comprises a highest value of 1 resembling accurate functioning of the PO sensor and a lowest value of 0 resembling failure of the PO sensor.

According to one embodiment herein, each of the AI, VI and GI is weighted according to a magnitude of decrease in accuracy between 1 and 0.

According to one embodiment herein, a detection and measurement of SpO2, PR and CoHb is done through a central unit, a PO reflectance sensor and an air bladder.

According to one embodiment herein, the method further comprises a computer readable program to assess rapid changes in gravitational forces in multiple directions simultaneously. The changes affect an accuracy to calculate the vibration index (VI).

According to one embodiment herein, the method further comprises a computer readable program and a barometer to measure a cabin pressure. A change in a cabin pressure affects an accuracy to calculate the altitude index (AI).

According to one embodiment herein, the method further comprises a three-dimensional accelerometer and a computer readable program to measure gravitational forces in at-least three directions (Gx, Gy and Gz. A magnitude of gravitational forces affects an accuracy to calculate the gravitational index (GI).

According to one embodiment herein, a pressure in the air bladder is adjusted on the basis of changes in gravitational forces in at-least three directions.

According to one embodiment herein, the method further comprises an early warning alarm. The early warning alarm is activated as an absolute value of the AI, GI and VI reaches a threshold point.

According to one embodiment herein, a data is collected through the PO sensor, stored and evaluated post flight, wherein the data is calculated in a real time and transmitted live to a ground control station and to the pilot via a heads-up display.

Figure 2:
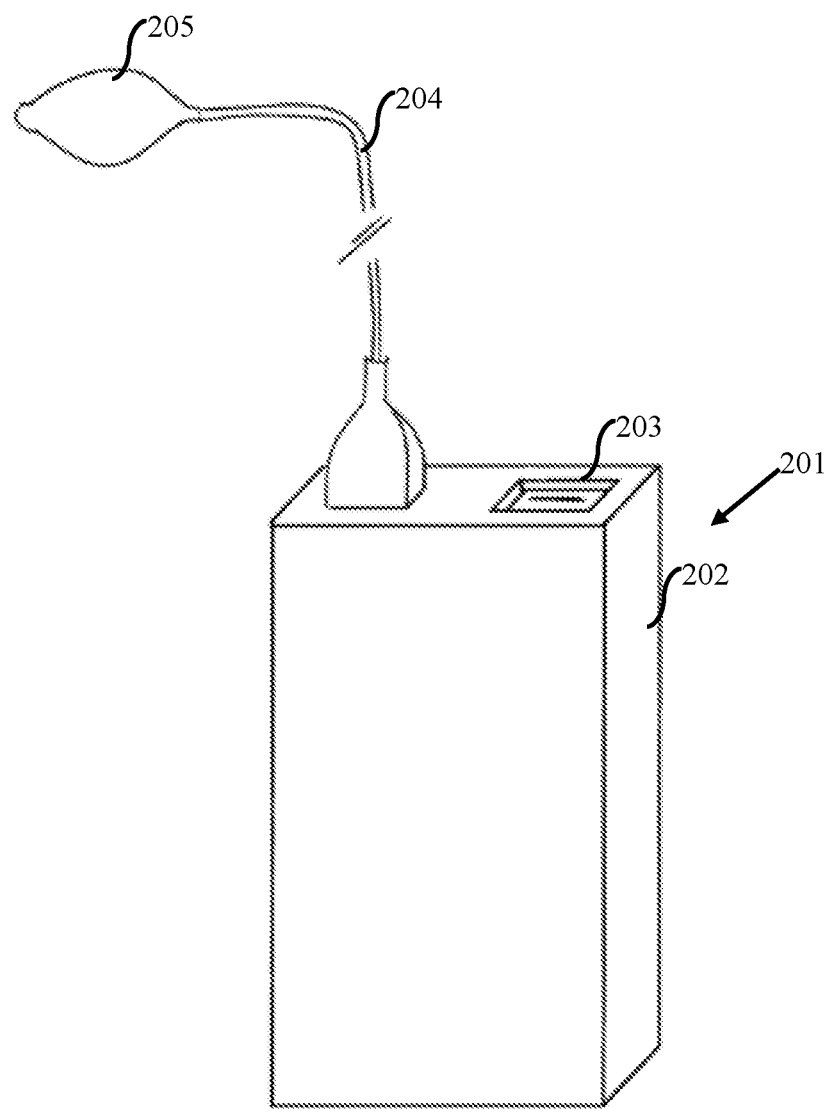
FIG. 2 illustrates a block diagram of a central unit with a pulse oximetry reflectance sensor, according to one embodiment herein.

FIG. 2 illustrates a block diagram of a central unit with a pulse oximetry reflectance sensor, according to one embodiment herein. With respect to FIG. 2, the central unit 201 is housed in a metal box 202 to fit in a front pocket of the aviator's (aircraft pilot) vest or to be placed in cockpit or cabin as a stand-alone. The central unit 201 comprises a Pulse Oximetry board, a barometer, an accelerometer, a data storage module and a rechargeable battery unit. The central unit 201 further comprises a data output port 203 and a connector 204 to the PO reflectance sensor 205.

Figure 3A:
FIGS. 3a and 3b illustrates a front view and a side view of an installation of the central unit, and the PO sensor in a helmet of an aircraft pilot, according to one embodiment herein.
Figure 3B:
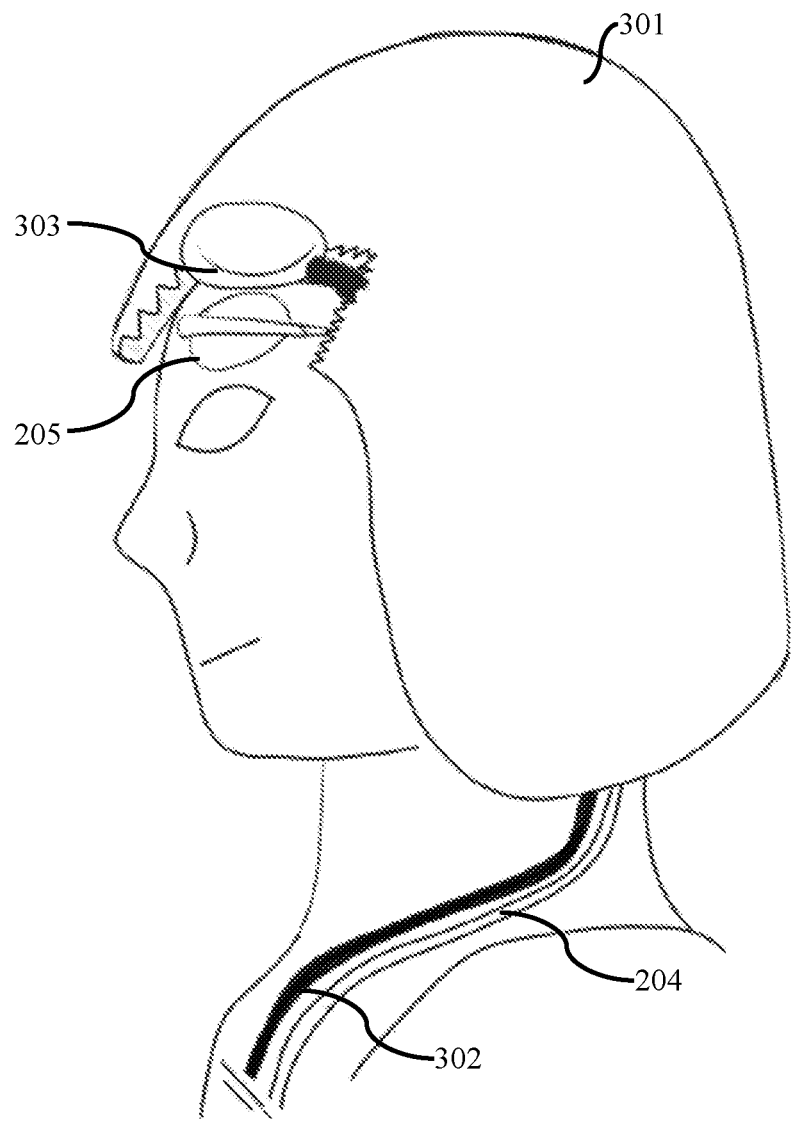

FIGS. 3a and 3b illustrates a front view and a side view of an installation of the central unit, and the PO sensor in a helmet of an aircraft pilot, according to one embodiment herein. With respect to FIG. 3a, the metal box 202 is placed in a front pocket or pouch of a combat vest of the aviator and the PO sensor 205 is routed behind an ear cup of the helmet 301 and placed in an optimal position above the eye and between the helmet and forehead of the aviator. With respect to FIG. 3b, the connector 204 to the PO sensor 205 and an air bladder hose 302 is routed behind the helmet ear cup 301 to an optimal position on the forehead above the eye and eye brow. The air bladder 303 is placed between the helmet 301 and the PO sensor 205 to apply increased pressure during inflation of the anti-gravity suit and increased gravitational forces.

According to one embodiment herein, the proposed Pulse Oximetry system contains a PO board (shall be approved by FDA) containing all the algorithms for SpO2, PR and COHb measurements. The algorithms further enable calculation of motion and vibration tolerance, low perfusion performance, alarms and indices of signal strength and signal quality. The PO system is powered by an internal rechargeable battery and have the capability of storing and transferring acquired data as well as a data output port to allow real-time data acquisition. The PO system further has a barometer or a pressure manometer for continuous monitoring of cabin pressure and a three-dimensional accelerometer for continuously monitoring direction and magnitude of G forces (Gx, Gy and Gz). The PO system also consist of a cable and forehead sensor placed in the headband of the pilot's helmet and held in place by a combination of padding, spring tension device and/or air bladder connected to a pressure source that is in concert with the anti-gravity systems, e.g., the anti-gravity suit ensemble or breathing regulator anti-gravity (BRAG). In helmets that are equipped with a separate bladder, the sensor bladder (air bladder) is connected to the existing bladder. The PO sensor exits the helmet and connected to a metal box containing the PO board, a data memory system, a power supply, a data output port, an accelerometer and a barometer.

It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the claims.

We claim:

1. A method for monitoring a non-invasive arterial oxygen saturation (SpO$_2$), a pulse rate (PR) and a level of carboxy-haemoglobin (COHb) in a blood flow of an aircraft pilot during an in-flight condition for detection of symptoms of hypoxia, wherein the method comprises the steps of:

detecting an arterial microcirculation of blood in a forehead of the aircraft pilot by using an infrared (IR) photometric technique;

installing a pulse oximetry (PO) reflectance sensor over an artery with microcirculation in the forehead, wherein the PO sensor is installed in a headgear of the aircraft pilot;

creating indices corresponding to an altitude index (AI), a vibration index (VI) and a gravitation index (GI) under a controlled condition of hypobaria as well as a varying condition of hypobaria;

creating a scale based on index values of the AI, VI and GI;

combining the index values of the AI, VI and GI with a signal strength value and a signal quality value of the PO sensor to calculate a weighted confidence index for SpO$_2$ (CI$_{sat}$) and a weighted confidence index for PR (CI$_{pr}$);

combining CI$_{sat}$ and CI$_{pr}$ to calculate an overall weighted confidence index (CI); wherein the value of CI determines an accuracy of measurements of SpO$_2$ and PR; and activating an early warning alarm as an absolute value of the AI, GI and VI reaches a threshold point.

2. The method as claimed in claim 1, wherein the scale comprises a highest value of 1 indicating accurate functioning of the PO sensor and a lowest value of 0 indicating failure of the PO sensor.

3. The method as claimed in claim 1, wherein each of the AI, VI and GI is weighted between 1 and 0 according to a magnitude of decrease in accuracy.

4. The method as claimed in claim 1, wherein a measurement of SpO2, PR and COHb is obtained using a central unit, a PO reflectance sensor and an air bladder.

5. The method as claimed in claim 4, wherein the central unit comprises a Pulse Oximetry board, a barometer, an accelerometer, a data storage module and a rechargeable battery unit.

6. The method as claimed in claim 4, wherein the central unit comprises a data output port and a connector to the PO reflectance sensor.

7. The method as claimed in claim 1, further comprising assessing rapid changes in gravitational forces in multiple dimensions simultaneously, wherein the changes affect an accuracy of calculating the vibration index (VI).

8. The method as claimed in claim 4, wherein the central unit comprises a barometer to measure a cabin pressure, wherein a change in the cabin pressure affects an accuracy of calculating the altitude index (AI).

9. The method as claimed in claim 4, wherein the central unit comprises a three-dimensional accelerometer to measure gravitational forces in at least three directions (Gx, Gy and Gz), wherein a magnitude of the gravitational forces affects an accuracy of calculating the gravitational index (GI).

10. The method as claimed in claim 4, wherein a pressure in the air bladder is adjusted on the basis of changes in gravitational forces in at least three directions.

11. The method as claimed in claim 1, further comprising storing data of the monitored SpO2, PR and COHb and evaluating it post flight, wherein the data is calculated in real time and transmitted live to a ground control station and to the pilot via a heads-up display.

* * * * *